United States Patent
Yamamoto et al.

(10) Patent No.: US 8,666,476 B2
(45) Date of Patent: *Mar. 4, 2014

(54) SURGERY ASSISTANCE SYSTEM

(75) Inventors: Seiji Yamamoto, Shizuoka-ken (JP);
Toshihisa Takai, Shizuoka-ken (JP);
Etsukazu Hayashimoto, Shizuoka-ken (JP); Akira Miura, Shizuoka-ken (JP)

(73) Assignee: National University Corporation Hamamatsu University School of Medicine, Shizuoka (JP)

( * ) Notice: Subject to any disclaimer, the term of this patent is extended or adjusted under 35 U.S.C. 154(b) by 63 days.

This patent is subject to a terminal disclaimer.

(21) Appl. No.: 13/203,820

(22) PCT Filed: Mar. 1, 2010

(86) PCT No.: PCT/JP2010/053250
§ 371 (c)(1),
(2), (4) Date: Aug. 29, 2011

(87) PCT Pub. No.: WO2010/101117
PCT Pub. Date: Sep. 10, 2010

(65) Prior Publication Data
US 2012/0004541 A1 Jan. 5, 2012

(30) Foreign Application Priority Data
Mar. 1, 2009 (JP) ................. 2009-047462

(51) Int. Cl.
A61B 5/05 (2006.01)

(52) U.S. Cl.
USPC ........... 600/424; 600/407; 600/427

(58) Field of Classification Search
USPC ....................................... 600/425
See application file for complete search history.

(56) References Cited

U.S. PATENT DOCUMENTS

| 4,506,676 | A | 3/1985 | Duska |
| 4,583,538 | A | 4/1986 | Onik et al. |

(Continued)

FOREIGN PATENT DOCUMENTS

| EP | 1982650 | 10/2008 |
| JP | 04-061848 | 2/1992 |

(Continued)

OTHER PUBLICATIONS

Office Action, Corresponding to U.S. Appl. No. 12/525,267, Mailed Sep. 27, 2011.

(Continued)

*Primary Examiner* — Jonathan G Cwern
*Assistant Examiner* — Amelie R Gillman
(74) *Attorney, Agent, or Firm* — Lathrop & Gage LLP

(57) ABSTRACT

Provided is a surgery assistance system to perform relatively fast and accurate alignment between three-dimensional surface shape data acquired by measurement using a three-dimensional surface shape scanner and three-dimensional internal shape data acquired in advance, even when the position of the patient and the surface shape of the skin of the patient change during the surgery. A surgery assistance system (1) includes a three-dimensional surface shape scanner (20) for acquiring three-dimensional surface shape data by measuring a three-dimensional surface shape of a patient (60) and a computing device (40) for processing the data from the three-dimensional surface shape scanner. The computing device stores therein three-dimensional internal shape data of the patient that is acquired in advance by measurement using a three-dimensional tomography scanner (30). The computing device has a unit that aligns the three-dimensional internal shape data and the three-dimensional surface shape data with each other by using data of a portion where a distance between a skeleton and a skin surface is small in the three-dimensional internal shape data and three-dimensional surface shape data corresponding to this portion.

18 Claims, 5 Drawing Sheets

(56) References Cited

U.S. PATENT DOCUMENTS

| | | | |
|---|---|---|---|
| 4,791,934 | A | 12/1988 | Brunnett |
| 5,107,839 | A | 4/1992 | Houdek et al. |
| 5,494,034 | A | 2/1996 | Schlondorff et al. |
| 5,531,520 | A | 7/1996 | Grimson et al. |
| 5,617,857 | A | 4/1997 | Chader et al. |
| 5,662,111 | A | 9/1997 | Cosman |
| 5,871,445 | A | 2/1999 | Bucholz |
| 6,135,946 | A | 10/2000 | Konen et al. |
| 6,285,902 | B1 | 9/2001 | Kienzle, III et al. |
| 6,377,839 | B1 | 4/2002 | Kalfas et al. |
| 6,490,475 | B1 | 12/2002 | Seeley et al. |
| 6,675,040 | B1 | 1/2004 | Cosman |
| 6,725,079 | B2 | 4/2004 | Zuk et al. |
| 8,112,144 | B2 | 2/2012 | Yamamoto et al. |
| 8,208,982 | B2 | 6/2012 | Miyakawa et al. |
| 8,251,893 | B2 | 8/2012 | Yamamoto et al. |
| 2001/0027272 | A1 | 10/2001 | Saito et al. |
| 2002/0128547 | A1 | 9/2002 | Furuhashi et al. |
| 2003/0000535 | A1 | 1/2003 | Galloway et al. |
| 2003/0130576 | A1 | 7/2003 | Seeley et al. |
| 2003/0163040 | A1 | 8/2003 | Gildenberg |
| 2004/0138556 | A1 | 7/2004 | Cosman |
| 2004/0210105 | A1 | 10/2004 | Hale et al. |
| 2005/0054910 | A1 | 3/2005 | Tremblay et al. |
| 2005/0182295 | A1 | 8/2005 | Soper et al. |
| 2005/0187432 | A1 | 8/2005 | Hale et al. |
| 2008/0051651 | A1* | 2/2008 | Yamamoto et al. ........... 600/437 |
| 2010/0094085 | A1 | 4/2010 | Yamamoto et al. |
| 2011/0054300 | A1 | 3/2011 | Yamamoto et al. |

FOREIGN PATENT DOCUMENTS

| | | |
|---|---|---|
| JP | 9-173352 | 7/1997 |
| JP | 9-511430 | 11/1997 |
| JP | 2000-350734 | 12/2000 |
| JP | 2001-066355 | 3/2001 |
| JP | 2001-204738 | 7/2001 |
| JP | 2001-293006 | 10/2001 |
| JP | 2002-263053 | 9/2002 |
| JP | 2003-088508 | 3/2003 |
| JP | 2003-254732 | 9/2003 |
| JP | 2005-278992 | 10/2005 |
| JP | 2007-209531 | 8/2007 |
| WO | WO 91/07726 | 5/1991 |
| WO | WO96/07144 | 3/1996 |
| WO | WO2008/093517 | 8/2008 |
| WO | WO2008/130361 | 10/2008 |

OTHER PUBLICATIONS

International Search Report (English and Japanese) corresponding to PCT/JP2010/053250, completed Mar. 15, 2010.

International Search Report, Corresponding to International Application No. PCT/JP2008/050139, Mailed Feb. 19, 2008.

Search Report, Corresponding to counterpart European Application No. 08703010.2, Mailed Jan. 17, 2011.

Colchester et al., (1996) "Development and preliminary evaluation of VISLAN, a surgical planning and guidance system using intra-operative video imaging," *Medical Image Analysis*, 1(1):73-90.

Shahidi et al., (2002) "Implementation, Calibration and Accuracy Testing of an Image-Enhanced Endoscopy System," *IEEE Transactions on Medical Imaging*, 21(12):1524-1535.

Yamashita et al. (1999) "Real-Time 3-D Model-Based Navigation System for Endoscopic Paranasal Sinus Surgery," *IEEE Transactions on Biomedical Engineering*, 46(1):107-116.

\* cited by examiner

SURGERY ASSISTANCE SYSTEM

FIELD OF THE INVENTION

The present invention relates to a surgery assistance system having a unit that aligns three-dimensional surface shape data acquired by measurement using a three-dimensional surface shape scanner and three-dimensional internal shape data acquired by measurement using a three-dimensional tomography scanner with each other, and also relates to an alignment method and an alignment program used in the surgery assistance system.

BACKGROUND OF THE INVENTION

Surgery assistance systems have been known which assist a surgeon by synthesizing and displaying a three-dimensional tomographic image captured by an X-ray CT apparatus or the like prior to a surgery and an image showing the front end position and the like of a surgical instrument inserted in the body. To synthesize the two images, data processing is needed that changes sets of coordinate data serving as the bases of the two images into sets of data sharing the same coordinate system. Hereinafter, data processing for changing two sets of coordinate data into sets of data sharing the same coordinate system will be simply referred to as data alignment. For example, Patent literature 1 and 2 describe the present inventors' surgery assistance systems, and describe techniques in which alignment is performed between the three-dimensional surface shape data acquired by measurement using a three-dimensional surface shape scanner and the three-dimensional internal shape data (three-dimensional tomographic data) acquired in advance by measurement using a three-dimensional tomography scanner. Patent literature 1 and 2 also describe techniques in which marker parts for detecting position and posture, which are attached to a surgical instrument, are measured using the three-dimensional surface shape scanner to calculate the position and posture of the surgical instrument, and then alignment is performed between the three-dimensional surface shape data of the patient and the coordinate data of the front end position of the surgical instrument. These techniques enable alignment between the three-dimensional internal shape data and the coordinate data of the front end position of the surgical instrument.

Techniques in Patent literature 3 and 4 are some other conventional techniques describing the synthesizing and displaying of a three-dimensional tomographic image and an image showing a specific part of a surgical instrument inserted in the body.

Patent literature 3 describes a technique in which a surgery navigation apparatus displays the orientation of the optical axis of a currently-used rigid endoscope on a three-dimensional tomographic image.

Patent literature 4 describes a technique using an endoscope that has distance measurement means (such as a triangulation method using spot-light irradiation or an ultrasonic sensor) for measuring the distance from the front end of an inserted part of the endoscope inserted in the patient's body to a surgical site inside the patient's body. By the technique, a location the endoscope is observing is determined and displayed on a CT/MRI image captured prior to the surgery.

According to Patent literature 3 and 4 described above, a three-dimensional surface shape scanner is not used to acquire the three-dimensional surface shape data of the patient and the position and posture of the endoscope. Instead, markers such as light emitting devices are attached to the patient and the endoscope, and the coordinates of these markers are detected by a position sensor. In the system, however, it is necessary to acquire the three-dimensional tomographic image with the markers on the patient, and also to acquire the relationships between the markers attached to the patient and characteristic points on the patient's face. Thus, inconvenience may be caused to the patient, and the system may become complicated. In addition, the accuracy of the synthesis may be deteriorated if the positions of the markers attached to the patient are changed. Accordingly, the surgery assistance systems using a three-dimensional surface shape scanner as described in Patent literature 1 and 2 can be said to be superior in terms of simpleness and accuracy.

Patemt Literature

[Patent literature 1] J Publication of Unexamined Patent Application No. 2007-209531

[Patent literature 2] International Patent Application Publication No. WO2008/093517

[Patent literature 3] Publication of Unexamined Patent Application No. 2001-293006

[Patent literature 4] Publication of Unexamined Patent Application No. 2001-204738

Problems to be Solved by the Invention

In the surgery assistance systems using a three-dimensional surface shape scanner as described in Patent literature 1 and 2, the patient is not fixed, and therefore the position of the patient varies minutely. For this reason, alignment between the three-dimensional surface shape data acquired by measurement using a three-dimensional surface shape scanner and the three-dimensional internal shape data (three-dimensional tomographic data) acquired in advance must be performed on a real time basis (at a predetermined, short time interval). However, since the skin is relatively soft, the skin may change its surface shape due to an influence of the insertion of the surgical instrument or an influence of the gravity. Such a change causes a problem of deteriorating the alignment accuracy.

The present invention has been made to solve the problem described above, and an object of the present invention is to provide a surgery assistance system capable of performing relatively fast and accurate alignment between the three-dimensional surface shape data acquired by measurement using a three-dimensional surface shape scanner and the three-dimensional internal shape data acquired in advance, even when the position of the patient and the surface shape of the skin of the patient change during the surgery.

Solution to Problems

To solve the problem described above, the present invention has the following structures.

A surgery assistance system includes a three-dimensional surface shape scanner that measures three-dimensional surface shape of a patient and acquires three-dimensional surface shape data, and a computing device that processes the data from the three-dimensional surface shape scanner.

The computing device stores therein three-dimensional internal shape data of the patient that is acquired in advance by measurement using a three-dimensional tomography scanner, and the computing device includes a unit that extracts data of a portion where a distance between a skeleton and a skin surface is small from the three-dimensional internal shape data, a unit that calculates a coordinate conversion factor by detecting three-dimensional surface shape data corresponding to the extracted three-dimensional internal shape data by matching from three-dimensional surface shape data acquired by the three-dimensional surface shape scanner, and a unit that aligns the three-dimensional internal shape data and the three-dimensional surface shape data with each other by using the calculated coordinate conversion factor.

A method for aligning three-dimensional surface shape data and three-dimensional internal shape data with each other, the three-dimensional surface shape data being acquired by measurement using a three-dimensional surface shape scanner and the three-dimensional internal shape data being acquired by measurement using a three-dimensional tomography scanner.

The method includes the steps of extracting data of a portion where a distance between a skeleton and a skin surface is small from the three-dimensional internal shape data, calculating a coordinate conversion factor by detecting three-dimensional surface shape data corresponding to the extracted three-dimensional internal shape data by matching from three-dimensional surface shape data acquired by the three-dimensional surface shape scanner, and aligning the three-dimensional internal shape data and the three-dimensional surface shape data with each other by using the calculated coordinate conversion factor.

A program for aligning three-dimensional surface shape data and three-dimensional internal shape data with each other, the three-dimensional surface shape data being acquired by measurement using a three-dimensional surface shape scanner, the three-dimensional internal shape data being acquired by measurement using a three-dimensional tomography scanner.

The program includes the steps of extracting data of a portion where a distance between a skeleton and a skin surface is small from the three-dimensional internal shape data, calculating a coordinate conversion factor by detecting three-dimensional surface shape data corresponding to the extracted three-dimensional internal shape data by matching from three-dimensional surface shape data acquired by the three-dimensional surface shape scanner, and aligning the three-dimensional internal shape data and the three-dimensional surface shape data with each other by using the calculated coordinate conversion factor.

Each configuration described above makes it possible to perform faster and more accurate alignment between the three-dimensional surface shape data acquired by measurement using the three-dimensional surface shape scanner and the three-dimensional internal shape data acquired by measurement using the three-dimensional tomography scanner, even when the position of the patient and the surface shape of the skin of the patient change during the surgery. Accordingly, the surgery assistance system can provide more accurate surgery navigation.

The present invention focuses on the fact that a movement of the patient and the insertion of a surgical instrument into the patient can hardly change the patient's skeleton such as the skull. Such a fact has led to: the extraction of three-dimensional internal shape data of a portion where the skin surface is as close as possible to the skeleton, the calculation of a coordinate conversion factor by detecting three-dimensional surface shape data corresponding to the extracted three-dimensional internal shape data by matching, and the alignment between the three-dimensional surface shape data and the three-dimensional internal shape data by using the coordinate conversion factor. The three-dimensional internal shape data is data that is obtained by measurement using a three-dimensional tomography scanner such as an X-ray CT or an MRI and so processed as to be indicative of the three-dimensional shape of the inside of the patient's body. So, the three-dimensional internal shape data has information of both the three-dimensional internal structure and the three-dimensional surface shape of the patient. As the method for extracting three-dimensional internal shape data of a portion where the skin surface is close to the skeleton, it is possible to perform data processing on whole three-dimensional internal shape data so as to automatically extract the portion where the distance between the skeleton and the skin surface is small. Alternatively, it is possible to extract the three-dimensional internal shape data by allowing the operator to view an image of the internal shape of the patient displayed based on given three-dimensional internal shape data, and to select a portion to be extracted on the image.

The alignment is performed as follows. One of the shape of the face obtained based on the extracted three-dimensional internal shape data and the shape of the face obtained based on the three-dimensional surface shape data is moved to match the other shape by changing the position and orientation of the coordinate axis. A coordinate conversion factor is calculated that is equivalent to a change of the coordinate axis in a state where the shapes of the face of the two sets of data best coincide with each other. Then, the calculated coordinate conversion factor is used to convert the coordinates of the one of the three-dimensional surface shape data and the three-dimensional internal shape data.

The alignment technique of the present invention is preferably used for update alignment (subtle alignment and coordinate error correction) that is performed during a surgery during which the surface shape of the patient's skin is likely to change. When initial alignment is performed before the surgery, the alignment may be performed using the shape data of the whole surface of the patient.

The present invention is preferably used for surgery assistance systems for surgeries requiring the insertion of a surgical instrument or an endoscope through the nostril. Note, however, that the present invention can be used not only for such surgery assistance systems but also for surgery assistance systems for other body parts. For example, the present invention can be used for surgery assistance systems for joints. The skull is preferably used as the aforementioned skeleton in a case of a surgery targeting the head or a surgery requiring the insertion of a surgical instrument or an endoscope through the nostril. In a case of a surgery on some other body part, a skeleton corresponding to that body part should be used. Meanwhile, the three-dimensional surface shape scanner may be any apparatus as long as it is able to measure the surface shape of the patient. For example, it is possible to use a three-dimensional surface shape scanner employing a phase shift method in which a grid pattern is projected using a xenon light or the like. The three-dimensional tomography scanner may be any apparatus as long as it is able to acquire three-dimensional internal shape data of the patient. For example, it is possible to use an X-ray CT apparatus, an MRI, or an ultrasonic diagnostic apparatus.

The present invention also has the following preferred forms.

The portion where the distance between the skeleton and the skin surface is small includes a portion of a face excluding a nasal portion and an ocular portion.

In addition, the portion where the distance between the skeleton and the skin surface is small includes cheekbone portions around eyeballs and a forehead portion.

The skin surfaces of the nasal portion and ocular portion of the face are likely to deform as they are remote from the skull serving as the skeleton. Hence, it is preferable to perform the alignment without these portions. The skin surfaces of the cheekbone portions around the eyeballs and the forehead portion are less likely to deform as they are close to the skull. Hence, it is preferable to perform the alignment by using these portions.

The present invention also has the following preferred form.

The three-dimensional surface shape data is acquired by the three-dimensional surface shape scanner occasionally at a predetermined time interval, and information having the three-dimensional internal shape data and the three-dimensional surface shape data aligned with each other is updated occasionally.

In the surgery assistance system using the three-dimensional surface shape scanner, the three-dimensional surface shape scanner measures the three-dimensional surface shape of the patient and the three-dimensional positions and postures of the surgical instrument and the like occasionally at a predetermined time interval. The three-dimensional surface shape data of the patient sent from the three-dimensional surface shape scanner and the three-dimensional internal shape data acquired and stored in advance are aligned occasionally. Accordingly, it is possible to provide surgery navigation enabling real-time displaying of the position of the front end and the like of the surgical instrument inserted in the body on three-dimensional tomographic images. The initial alignment is performed before the surgery by using the three-dimensional surface shape data of the patient and the three-dimensional internal shape data acquired in advance. The update alignment is performed during the surgery by using the three-dimensional surface shape data of the patient and a pre-extracted part (a portion where the distance between the skeleton and the skin surface is small) of the three-dimensional internal shape data. In this way, the speed of data processing for the update alignment can be increased, thereby improving the real time performance.

Advantages of the Invention

With above configurations, the present invention enables a surgery assistance system to perform relatively fast and accurate alignment between three-dimensional surface shape data acquired by measurement using a three-dimensional surface shape scanner and three-dimensional internal shape data acquired in advance, even when the position of the patient and the surface shape of the skin of the patient change during the surgery.

DESCRIPTIONS OF THE INVENTION

A preferred embodiment of a surgery assistance system of the present invention will be described below with reference to drawings.

Figure 1:
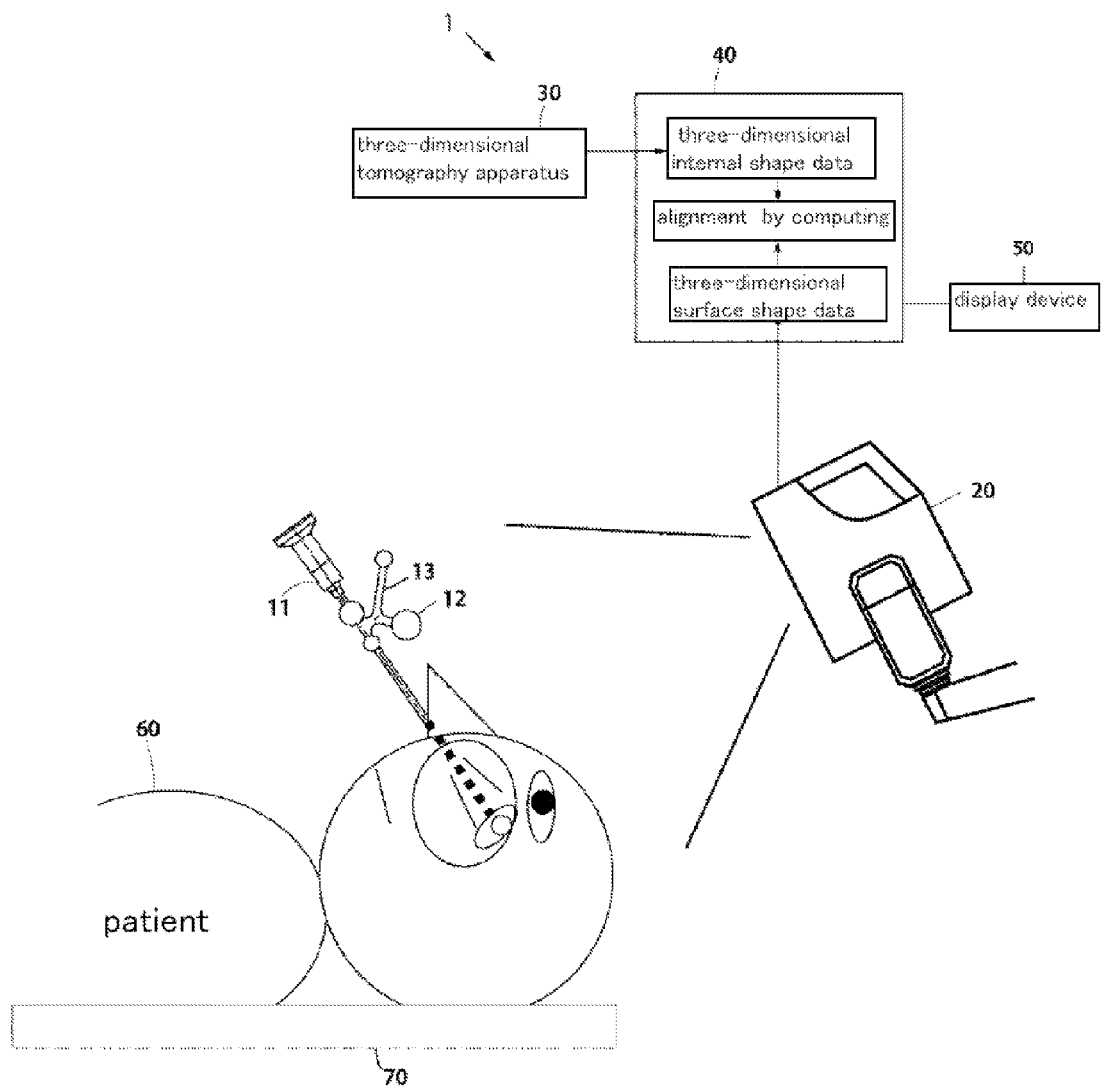
FIG. 1 is a schematic diagram of a surgery assistance system in an embodiment of the present invention.

FIG. 1 is a configuration diagram schematically showing the embodiment of the surgery assistance system of the present invention. A surgery assistance system 1 is a device that provides a surgeon and the like with information such as the front end position of a surgical instrument inside the body of the patient 60 or the observing site of an endoscope during a surgery on a patient 60. Surgeries using the surgery assistance system 1 in this embodiment include, for example, otorhinolaryngological surgeries such as an endoscopic surgery on the paranasal sinuses.

As shown in FIG. 1, the surgery assistance system 1 is configured to include a surgical instrument 11 such as a rigid endoscope, marker part 12, a three-dimensional surface shape scanner 20, a three-dimensional tomography apparatus (three-dimensional internal shape scanner) 30 such as an X-ray CT, an MRI, or the like, a computing device 40 such as a PC and a display device 50 such as a monitor. The surgical instrument 11 is an instrument that is manipulated by a surgeon and inserted into the body of the patient 60.

The marker part 12 is an object that is provided fixed at positions having predetermined positional relationships with the surgical instrument 11, and is capable of defining three or more fixed points. The marker part 12 is scanned by the three-dimensional surface shape scanner 20. Data thus obtained is used to acquire the three-dimensional coordinates (three-dimensional surface shape data) of multiple points on the surface thereof. The three-dimensional coordinates of the multiple points are then used to acquire the coordinate of the spherical center. To be specific, the marker part 12 is differently-sized spherical member fixed to the surgical instrument 11 through support members 13, respectively. The sizes are made different because acquiring the diameters of the spherical objects on the basis of the three-dimensional coordinates (three-dimensional surface shape data) of multiple points on the surfaces thereof acquired by the three-dimensional surface shape scanner 20 allows the center coordinates of the spherical objects to be found distinguishable from one another. The marker part 12 is provided to the surgical instrument 11 at positions rearward of a part to be inserted into the patient 60, i.e., positions where the surgical instrument 11 is not inserted into the patient 60. Note that the marker part 12 provided to the surgical instrument 11 only needs to be such objects that the coordinates of three or more fixed points can be found distinguishable from one another by using the three-dimensional coordinates (three-dimensional surface shape data) of multiple points on the surfaces acquired by the three-dimensional surface shape scanner 20. Hence, the marker parts 12 do not necessarily need to be spherical as in this embodiment.

The three-dimensional surface shape scanner 20 is an apparatus that performs three-dimensional scan on the surface of the patient 60 and the marker parts 12 and outputs data that serves as a base for calculating three-dimensional surface shape data. The three-dimensional surface shape scanner 20 performs such actions occasionally at a preset time interval during a surgery requiring the insertion of the surgical instrument 11 into the patient 60. As shown in FIG. 1, in a case of inserting the surgical instrument 11 through the nostril of the patient 60, the three-dimensional surface shape scanner 20 is provided at such a position as to be able to capture the face of the patient 60 and the marker parts 12. The three-dimensional surface shape scanner 20 is connected to the computing device 40 and sends the computing device 40 the data that is obtained through the scan and that serves as a base for calculating three-dimensional surface shape data.

The data that is sent from the three-dimensional surface shape scanner 20 and that serves as a base for calculating three-dimensional surface shape data is processed by the computing device 40 to calculate the three-dimensional coordinates (three-dimensional surface shape data) of multiple points on the surface of the scanned objects. As the three-dimensional surface shape scanner 20, it is possible to use an apparatus employing a phase shift method which is described in Japanese Patent Application Publication No. 2003-254732, for example. This is a method in which three-dimensional scan is performed by projecting a grid pattern onto a measuring object and receiving reflected light beams therefrom while moving the grid pattern. White light beams emitted from a xenon light, for example, which are similar to natural sunlight may be used to project the grid pattern. In this way, the light beams can hardly affect the measuring object.

Meanwhile, it is possible to measure the three-dimensional surface shape of a measuring object in a measurement time of 1 second from a distance of 90±10 cm by using Fscan of PULSTEC INDUSTRIAL CO., LTD which is a three-dimensional surface shape scanner employing the phase shift method. In addition to the measurement of the three-dimensional surface shape of a measuring object, it is also possible to acquire color information by capturing an image of the measuring object. That is, data for displaying a surface shape with a color image can be acquired in 1 second. Now, suppose that three-dimensional surface shape data acquired through the above measurement is subjected to data processing, and the lengths of a given part of each of the measuring objects (e.g., the diameter of each of spherical objects) is calculated. In this case, the measurement accuracy falls within a range of 0.1 to 0.6 mm. The measuring objects can be distinguished from one another if the length of the given part is slightly different from one measuring object to another. Moreover, the light beams used to project the grid pattern are white light beams having approximately 28% of an illuminance obtained in a cloudy day (outside) during daylight, hence requiring no use of a laser or the like. Thus, the three-dimensional surface shape data of the human body can be acquired safely.

The three-dimensional tomography apparatus 30 acquires three-dimensional internal shape data (three-dimensional tomographic data) of the patient 60 into which the surgical instrument 11 is to be inserted. The three-dimensional tomography apparatus 30 may be any apparatus as long as it is able to acquire three-dimensional internal shape data (three-dimensional tomographic data) of the patient. A preexisting apparatus such as an X-ray CT, an MRI, an ultrasonic, or a PET may be used. Three-dimensional internal shape data acquired by the three-dimensional tomography apparatus 30 is taken in by the computing device 40. Note that the three-dimensional tomography apparatus 30 does not need to be installed in the same location as the three-dimensional surface shape scanner 20 and the computing device 40. The three-dimensional scan by the three-dimensional surface shape scanner 20 is performed usually separately from the acquisition of the three-dimensional internal shape data by the three-dimensional tomography apparatus 30. Meanwhile, a method described, for example, in Japanese Patent Application Publication No. 2005-278992 may be used as a method for constructing three-dimensional shape information from a set of two-dimensional tomographic image data such as CT images acquired by the three-dimensional tomography apparatus 30.

The computing device 40 is a device that takes in data acquired through scan by the three-dimensional surface shape scanner 20 and serving as a base of three-dimensional surface shape data, and also takes in three-dimensional internal shape data of the patient 60 acquired by the three-dimensional tomography apparatus 30, and then performs information processing on these pieces of information. The computing device 40 is configured, for example, by a PC (Personal Computer) or the like. The computing device 40 performs alignment between the three-dimensional internal shape data measured and stored in advance by the three-dimensional tomography apparatus 30 and the three-dimensional surface shape data measured on a real time basis (at a predetermined time interval) by the three-dimensional tomography apparatus 30, upon every input of the three-dimensional surface shape data. This alignment is done by calculating a coordinate conversion factor for converting two sets of data into sets of data sharing the same coordinate system and converting the coordinates of the two sets of data by use of the coordinate conversion factor. This coordinate conversion factor is calculated by detecting, in the inputted three-dimensional surface shape data, three-dimensional surface shape data corresponding to the pre-stored and -extracted three-dimensional internal shape data by matching. An arithmetic algorithm for the calculation of the coordinate conversion factor based on matching between the two sets of shape data is described specifically in the conventional techniques International Patent Application Publication No. WO2008/093517 and Japanese Patent Application Publication No. 2007-209531, and the like. Navigation images are created using the internal shape data and surface shape data of the patient, the position and posture data of the surgical instrument, the optical-axis data of the rigid endoscope, and the like on the basis of the result obtained by the alignment. Such navigation images, or in particular images showing the internal shape of the patient with the front end of the surgical instrument and the observing site of the rigid endoscope presented thereon, are displayed on the display device 50 to thereby provide surgery navigation.

Figure 2:
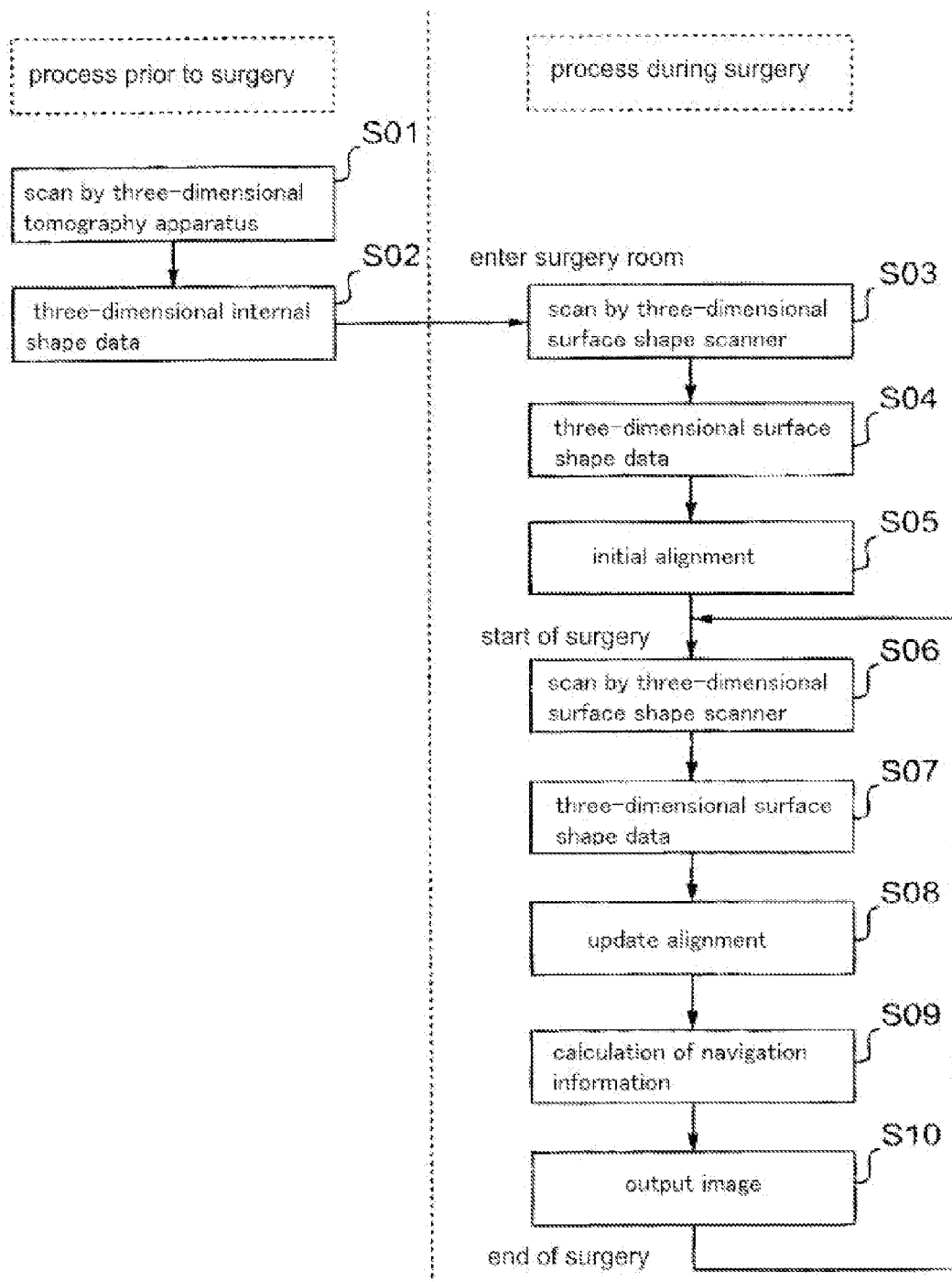
FIG. 2 is a flowchart for the surgery assistance system in the embodiment of the present invention.

Next, an operation of the surgery assistance system 1 will be described with reference to a flowchart in FIG. 2. The operation is an operation performed when a surgery is conducted on the patient 60 by inserting the surgical instrument 11. In this description, the operation will be described separately as a process prior to the surgery and a process during the surgery.

First, prior to the surgery, the three-dimensional tomography apparatus 30 is used to perform preoperative CT scan on the patient 60 (S01). This preoperative CT scan is performed on a region including the part of the patient 60 into which the surgical instrument 11 is to be inserted. As a result, there is acquired three-dimensional internal shape data of the patient 60 including the face, i.e., the surface of the patient 60 and the part of the patient 60 into which the surgical instrument 11 is to be inserted. The three-dimensional internal shape data acquired through the CT scan by using the three-dimensional tomography apparatus 30 is taken in to the computing device 40 and saved in storage unit in the computing device 40. Then, three-dimensional internal shape data of a portion where the distance between the skeleton and the skin surface is small is extracted either automatically or by use of a setting defined by an operator, and then is saved in other area of the storage unit (S02). The process described above is the process prior to the surgery, and is performed, for example, on the day before the surgery or the like.

Figure 3:
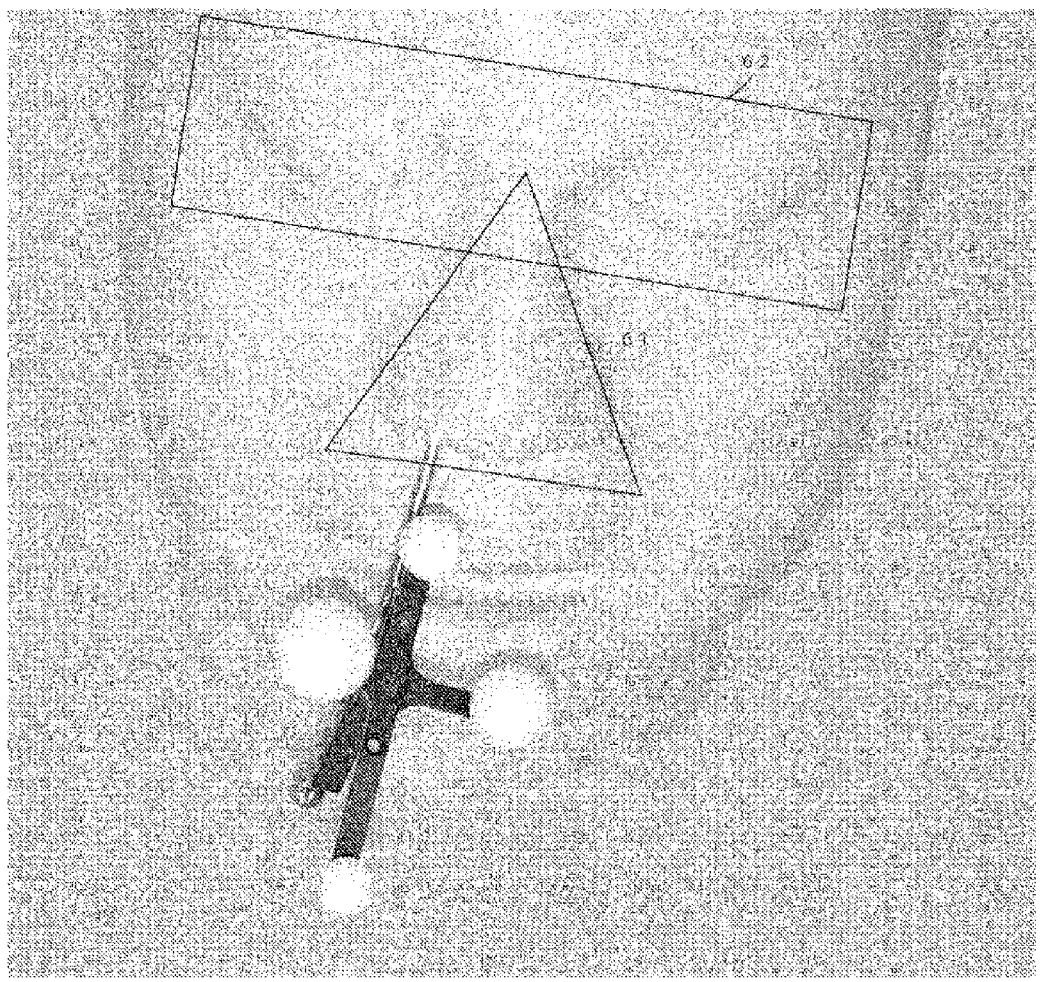
FIG. 3 shows examples of a deformable portion.
Figure 4:
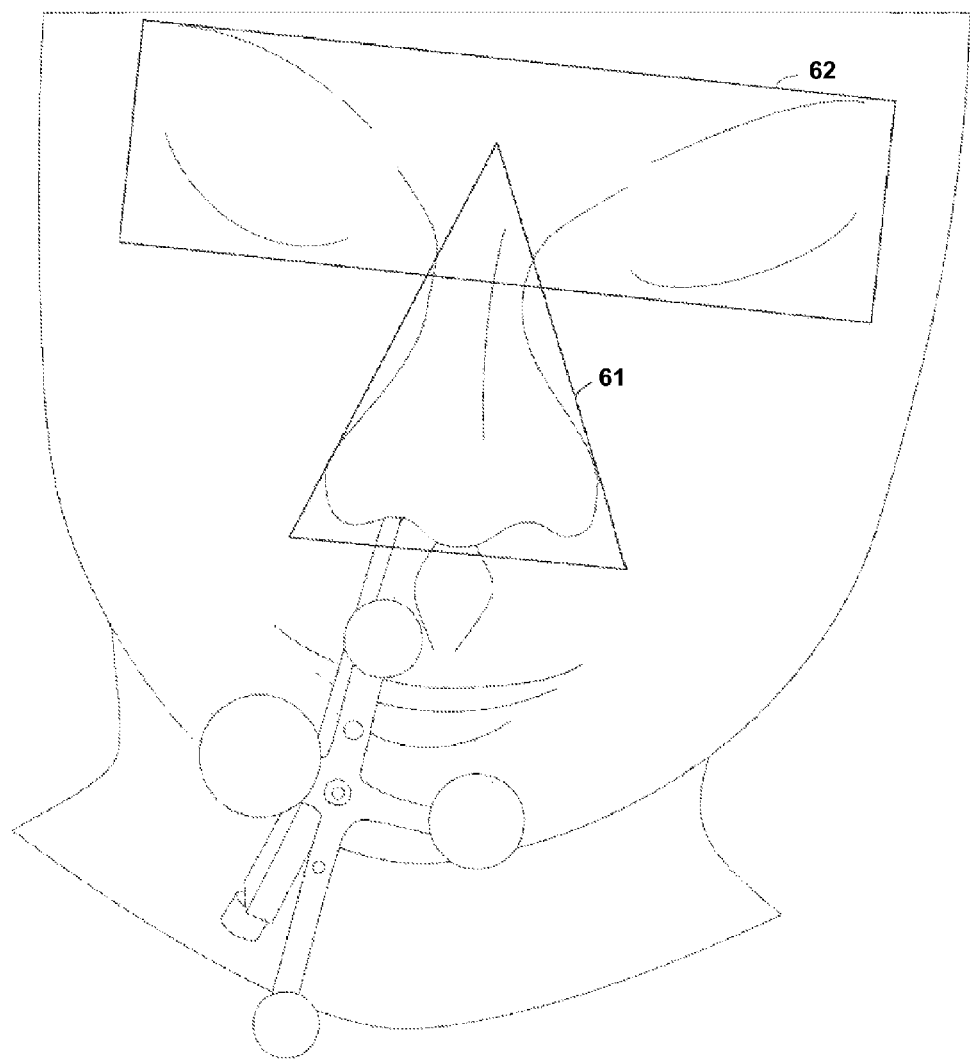
FIG. 4 shows the examples of the deformable portion (trace of FIG. 3)
Figure 5:
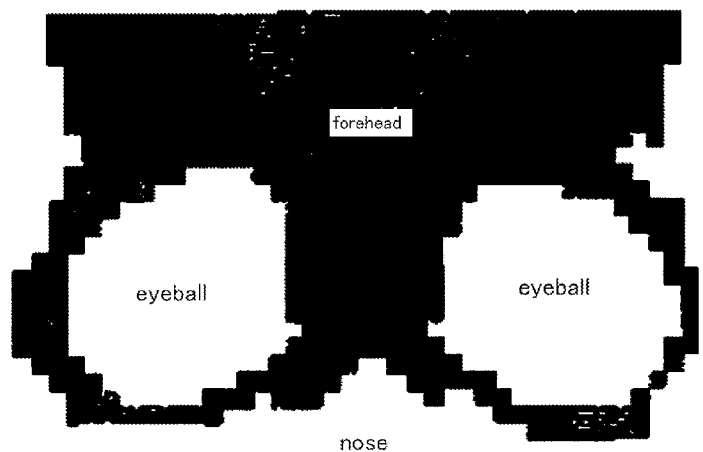
FIG. 5 shows examples of a portion suitable for alignment.

Now, the three-dimensional internal shape data of the portion where the distance between the skeleton and the skin surface is small is described. A nose portion 61 and an ocular portion 62 in the face have large distances between the skeleton and the skin surface as shown particularly in FIGS. 3 and 4, and are therefore likely to receive an influence of the gravity attributable to a movement of the patient 60 and an influence of the insertion of the surgical instrument 11. For this reason, it is preferable to perform alignment by using a portion of or the whole face excluding nose portion 61 and an ocular portion 62. Note that FIG. 4 is a trace of FIG. 3 created for the purpose of making the contour more noticeable. FIG. 5 shows preferable examples of the portion where the distance between the skeleton and the skin surface is small. Cheekbone portions around the eyeballs and a forehead portion have small distances between the skeleton (skull) and the skin surface, and are therefore affected less by deformation attributable to a movement of the patient and the insertion of the surgical instrument. Hence, those portions are preferable for the calculation of a coordinate conversion factor to be used for alignment. Note that if the patient is covered with a sheet, it is impossible to acquire three-dimensional surface shape data of the portion covered with the sheet. In this case, a portion of the patients shown in FIG. 5, which is not covered with the sheet, is used.

Next, the process during the surgery will be described. First, the patient 60 enters a surgery room and is placed supine on a surgical table 70 so that the surgical instrument 11 can be inserted through the nostril as shown in FIG. 1. After the patient 60 is placed but before the surgical instrument 11 is inserted, the three-dimensional surface shape scanner 20 scans patient 60 which is placed (S03). Data obtained through the scan is sent from the three-dimensional surface shape scanner 20 to the computing device 40. The computing device 40 in turn calculates the three-dimensional surface shape data of the patient 60.

Subsequently, initial alignment is performed between the three-dimensional internal shape data having been stored and the three-dimensional surface shape data obtained through the scan (S04). This initial alignment is performed before the surgery. Since this alignment is the first alignment, the alignment is performed by using the three-dimensional internal shape data of the whole face of the patient (shape data of portions with characteristic shapes such as the nose in particular) and the three-dimensional surface shape data. The alignment method is performed by calculating a coordinate conversion factor by matching between the shape of the face obtained from the three-dimensional internal shape data and the shape of the face obtained from the three-dimensional surface shape data. The method is described in International Patent Application Publication No. WO2008/093517, Japanese Patent Application Publication No. 2007-209531, and the like, and thus detailed description thereof is omitted here. Note that if the alignment accuracy can be secured sufficiently, the initial alignment may be performed by using the three-dimensional internal shape data of the portion where the distance between the skeleton and the skin surface is small (thin-skinned portion).

Subsequently, the surgery starts, and the surgeon inserts the surgical instrument 11 into the patient 60. The three-dimensional surface shape scanner 20 continues to scan the patient 60 and the marker parts 12 even after the surgical instrument 11 is inserted into the patient 60 (S06). Data obtained by the scan is sent from the three-dimensional surface shape scanner 20 to the computing device 40. The computing device 40 in turn calculates three-dimensional surface shape data (S07).

Subsequently, update alignment is performed between the three-dimensional surface shape data acquired in S07 and the three-dimensional internal shape data stored in advance (S08). Alignment has already been done by the initial alignment in S05, but the position of the patient changes during the surgery. Thus, the update alignment in S08 is performed by re-calculating a coordinate conversion factor to be used for another data alignment and aligning the sets of data by use of the newest coordinate conversion factor. In this update alignment, the coordinate conversion factor is calculated by detecting, in the three-dimensional surface shape data acquired in S07, the three-dimensional surface shape data corresponding to the already-extracted and -stored three-dimensional internal shape data of the portion where the distance between the skeleton and the skin surface is small by matching. The calculated coordinate conversion factor is used to perform the data alignment. A movement of the patient and the insertion of the surgical instrument into the patient can hardly change the skeleton or the skin surface of the portion where the distance between the skeleton and the skin surface is small. Hence, the data alignment can be performed with high accuracy by using the coordinate conversion factor calculated in the above manner. Moreover, the three-dimensional internal shape data that has been extracted and stored is data constituting a part of the whole three-dimensional internal shape data. Hence, data processing for the matching can be performed at a high speed. Accordingly, the data alignment can be performed at a high speed. Note that this data alignment is performed not only for the three-dimensional surface shape data and the three-dimensional internal shape data, but also for the coordinate of the front end of the surgical instrument 11 and, if the surgical instrument 11 is a rigid endoscope, for position data of the optical axis.

Figure 6:
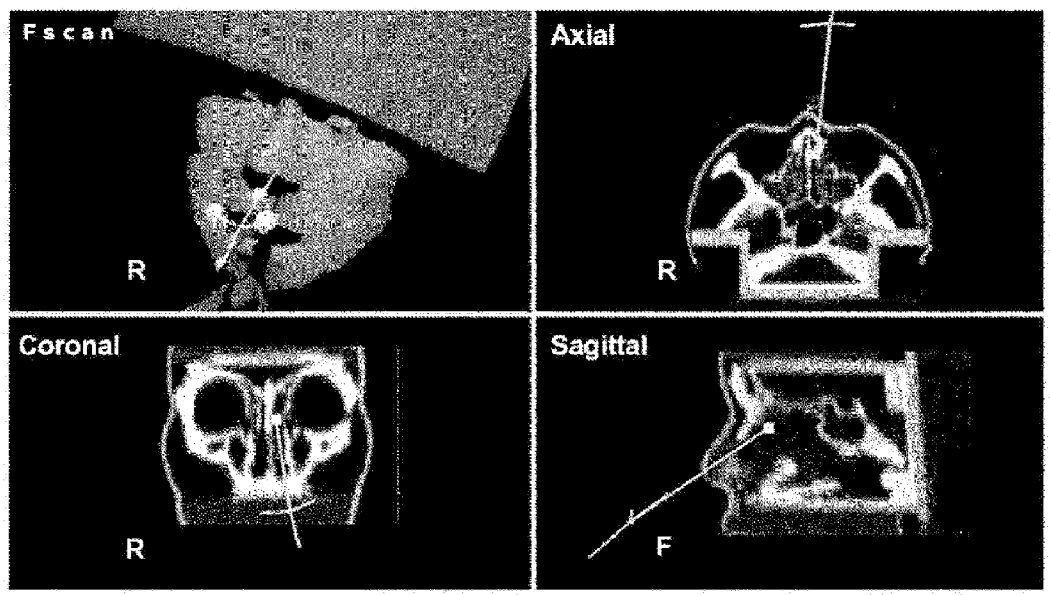
FIG. 6 is display example 1 of a surgery navigation screen.

Subsequently, navigation information is created based on the aligned information (S09). As shown in FIG. 6, the navigation information is a set of navigation images which are images showing the internal shape of the patient with the front end and the like of the surgical instrument 11 presented thereon. In a case where the surgical instrument 11 is a rigid endoscope, the navigation information is a set of navigation images which shows the internal shape of the patient with the observed site and the like of the rigid endoscope presented thereon. The created navigation information, an endoscopic image, and the like are displayed on the display device 50 (S10). FIG. 6 shows examples of a display on the display device 50. S06 to S10 are repeated during the surgery at a predetermined short time interval, and the alignment and the display of the navigation information on the display device 50 are performed on a real time basis.

Although, an exemplary embodiment of the present invention has been described, needless to say that the present invention is not limited to the embodiment and various changes can be made without departing from the technical concepts described in the scope of claims.

EXPLANATION OF SYMBOL

1: surgery assistance system
11: surgical instrument (rigid endoscope)
12: marker part
13: support member
20: three-dimensional surface shape scanner
30: three-dimensional tomography apparatus
40: computing device
50: display device
60: patient
61: nose portion
62: ocular portion
70: surgical table

What is claimed is:
1. A surgery assistance system comprising:
a surgical instrument having a marker part and a front end configured for insertion into a patient;
a three-dimensional surface shape scanner that measures three-dimensional surface shape of a patient and acquires three-dimensional surface shape data, wherein the three-dimensional surface shape data includes a three-dimensional position of the marker part, and a computing device that processes the data from the three-dimensional surface shape scanner, wherein
three-dimensional internal shape data of the patient that is acquired in advance by measurement using a three-dimensional tomography scanner is stored in the computing device, and
the computing device includes a unit that extracts data of a portion where a distance between a skeleton and a skin surface is small and includes a portion of a face excluding a nasal portion and an ocular portion from the three-dimensional internal shape data, a unit that calculates a coordinate conversion factor by detecting three-dimensional surface shape data corresponding to the extracted three-dimensional internal shape data by matching from three-dimensional surface shape data acquired by the three-dimensional surface shape scanner, and a unit that aligns the three-dimensional internal shape data and the three-dimensional surface shape data with each other by using the calculated coordinate conversion factor; wherein the computing device provides a real-time position of the surgical instrument front end in the patient even when the patient position and patient surface shape changes during a surgery.

2. The surgery assistance system according to claim 1, wherein the portion where the distance between the skeleton and the skin surface is small includes cheekbone portions around the eye.

3. The surgery assistance system according to claim 2, wherein the portion where the distance between the skeleton and the skin surface is small is a forehead portion.

4. The surgery assistance system according to any one of claims 1 to 3, wherein the three-dimensional surface shape data is acquired by the three-dimensional surface shape scanner occasionally at a predetermined time interval, and information for aligning three-dimensional internal shape data and the three-dimensional surface shape data with each other is updated occasionally.

5. The surgery assistance system of claim 1, wherein:
the marker part defines at least three fixed points that are scanned by the three-dimensional surface shape scanner, wherein the marker part remains outside the patient during surgery.

6. The surgery assistance system of claim 5, wherein the three-dimensional surface shape scanner captures the patient face and the at least three fixed points of the marker part.

7. The surgery assistance system of claim 1, wherein the surgical instrument comprises a rigid endoscope configured for insertion through a nostril.

8. A method for aligning a three-dimensional surface shape data and a three-dimensional internal shape data with each other, the method comprising the steps of:
acquiring the three-dimensional surface shape data by measurement using a three-dimensional surface shape scanner;
acquiring the three-dimensional internal shape data by measurement using a three-dimensional tomography scanner and storing the three-dimensional internal shape date in a computing device,
providing the three-dimensional surface shape data to the computing device;
extracting data from the computing device of a portion where a distance between a skeleton and a skin surface is small and includes a portion of a face excluding a nasal portion and an ocular portion from the three-dimensional internal shape data,
calculating a coordinate conversion factor by detecting three-dimensional surface shape data corresponding to the extracted three-dimensional internal shape data by matching from three-dimensional surface shape data acquired by the three-dimensional surface shape scanner, wherein the three-dimensional surface shape data includes a three-dimensional position of a marker part connected to a surgical instrument,
aligning the three-dimensional internal shape data and the three-dimensional surface shape data with each other by using the calculated coordinate conversion factor; and
displaying a front end position of a surgical instrument inserted in a patient, wherein the aligning step accommodates a change in position of the patient and surface shape of the patient during surgery.

9. The method of claim 8 used with a surgical procedure on a patient.

10. The method of claim 9, wherein the patient changes position or the skin deforms during the surgical procedure.

11. The method of claim 10, wherein the surgical procedure is an otorhinolaryngological procedure.

12. The method of claim 11 further comprising an updating alignment step to accommodate changes in patient position during the surgical procedure.

13. The method of claim 10, wherein the surgical procedure comprises endoscopic surgery.

14. The method of claim 13, further comprising the step of acquiring a three-dimensional position of each of at least three or more fixed points of a marker part that is connected to a surgical instrument with the three-dimensional surface shape scanner.

15. The method of claim 14, wherein the surgical instrument is positioned relative to the face of the patient so that the three-dimensional surface shape scanner captures the face of the patient and the marker parts.

16. The method of claim 8, wherein the three-dimensional surface shape data is acquired without a laser.

17. The method of claim 8, wherein the extracting data is from a portion of a face excluding a nasal portion and an ocular portion.

18. A program embodied on a non-transitory computer readable medium for aligning three-dimensional surface shape data and three-dimensional internal shape data of a patient with each other, the three-dimensional surface shape data being acquired by measurement using a three-dimensional surface shape scanner, wherein the three-dimensional surface shape data includes a three-dimensional position of a marker part connected to a surgical instrument, the three-dimensional internal shape data being acquired by measurement using a three-dimensional tomography scanner, the program having the steps of:
extracting data of a portion where a distance between a skeleton and a skin surface is small and includes a portion of a face excluding a nasal portion and an ocular portion from the three-dimensional internal shape data, calculating a coordinate conversion factor by detecting three-dimensional surface shape data corresponding to the extracted three-dimensional internal shape data by matching from three-dimensional surface shape data acquired by the three-dimensional surface shape scanner, aligning the three-dimensional internal shape data and the three-dimensional surface shape data with each other by using the calculated coordinate conversion factor; and providing a position of a front end of a surgical instrument inserted in a patient for display even when patient position and surface shape changes during a surgery.

* * * * *